(12) United States Patent
Hutton et al.

US006475723B2

(10) Patent No.: US 6,475,723 B2
(45) Date of Patent: *Nov. 5, 2002

(54) PATHOGENIC TAU MUTATIONS

(75) Inventors: Michael L. Hutton, Jacksonville Beach, FL (US); Peter Heutink, Rotterdam (NL); Alison M. Goate, St. Louis, MO (US); Stuart M. Brown, Buxton (GB)

(73) Assignees: Mayo Foundation for Medical Education and Research, Rochester, MN (US); Washington University, St. Louis, MO (US); Erasmus Universiteit Rotterdam (NL); The Victoria University of Manchester (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/302,964

(22) Filed: Apr. 30, 1999

(65) Prior Publication Data

US 2002/0026651 A1 Feb. 28, 2002

Related U.S. Application Data

(60) Provisional application No. 60/097,492, filed on Aug. 21, 1998, provisional application No. 60/087,942, filed on Jun. 4, 1998, and provisional application No. 60/083,791, filed on May 1, 1998.

(51) Int. Cl.[7] .......................... C12Q 1/68; C12P 19/34; C07H 21/04
(52) U.S. Cl. ................. 435/6; 435/91.1; 435/91.2; 536/23.5
(58) Field of Search ................ 800/18, 8; 536/23.1, 536/24.33, 23.5; 435/320.1, 91.2, 440, 6, 7.1, 91.1

(56) References Cited

U.S. PATENT DOCUMENTS 5,958,684 A * 9/1999 VanLeeuwen et al. ......... 435/6

FOREIGN PATENT DOCUMENTS

| WO | WO 97/27296 | 7/1997 |
| WO | WO 97/48792 | 12/1997 |
| WO | WO 98/01549 | 1/1998 |
| WO | WO 98/17782 | 4/1998 |

OTHER PUBLICATIONS

Conrad et al. Ann. Neurology 41(2):277–281, Feb. 1997.*
Ebert et al. Molecular Endocrinology 2(3):277–283, Mar. 1988.*
Hammer et al. Journal of Animal Science 63(1):269–278, Jul. 1986.*
Mullins et al. Journal of Clinical investigation 87(7):1557–1560, Apr. 1996.*
Wall et al. Journal of Dairy Science 80:2213–2224, Sep. 1997.*
Roks et al. Neuroscience Letters 277(2):137–139, Dec. 1999.*
Andreadis et al., "Structure and Novel Exons of the Human I Gene", *Biochemistry*, 31(43)10626–10633 (1992).
Arrasate et al., "Polymerization of Tau Peptides into Fibrillar Structures. The Effect of FTDP–17 Mutations", *FEBS Letters*, 446:199–202 (1999).
Baker et al., "Localization of Frontotemporal Dementia with Parkinsonism in an Australian Kindred to Chromosome 17q21–22", *Ann. Neurol.*, 42(5):794–798 (1997).
Dayanandan et al., "Mutations in Tau Reduce its Microtubule Binding Properties in Intact Cells and Affect its Phosphorylation", *FEBS Letters*, 446:228–232 (1999).
Foster et al., "Frontotemporal Dementia and Parkinsonism Linked to Chromosome 17: A Consensus Conference", *Ann. Neurol.*, 41(6):706–715 (Jun. 1997).
Froleich et al., "Mapping of a Disease Locus for Familial Rapidly Progressive Frontotemporal Dementia to Chromosome 17q12–21", *Amer. J. Med. Genet.*, 74:380–385 (1997).
Heutink et al., "Hereditary Frontotemporal Dementia is Linked to Chromosome 17q21–q22: A Genetic and Clinicopathological Study of Three Dutch Families", *Ann. Neurol.*, 41(2):150–159 (1997).
Hutton et al., "Association of Missense and 5'–Splice–Site Mutations in *tau* with the Inherited Dementia FTDP–17", *Nature*, 393:702–705 (1998).
Ingelson et al., "Microtubule–Associated Protein Tau in Human Fibroblasts with the Swedish Alzheimer Mutation", *Neuroscience Letters*, 220:9–12 (1996).
Jicha et al., "Sequence Requirements for Formation of Conformational Variants of Tau Similar to Those Found in Alzheimer's Disease", *J. Neurosci. Res.*, 55:713–723 (1999).
Leger et al., "Conversion of Serine to Asparate Imitates Phosphorylation Induced Charges in the Structure and Function of Microtubule–Associated Protein Tau", *J. Biol. Chem.*, 272(13):8441–8446 (1997).
Mirra et al., "Tau Pathology in a Family with Dementia and a P301L Mutation in Tau", *J. Neuropath. Exp. Neurol.*, 58(4):335–345 (1999).
Murrell et al., "Familial Multiple–System Tauopathy with Presenile Dementia is Localized to Chromosome 17", *Am. J. Hum. Genet.*, 61(5):1131–1138 (1997).

(List continued on next page.)

*Primary Examiner*—Deborah Crouch
*Assistant Examiner*—Joseph Woitach
(74) *Attorney, Agent, or Firm*—Fish & Richardson, P.C., P.A.

(57) ABSTRACT

Isolated nucleic acid molecules that include a tau gene sequence are described. The tau gene sequences have a mutation linked to a Tau pathology. Transgenic non-human mammals containing a Tau pathology also are also described.

26 Claims, 4 Drawing Sheets

OTHER PUBLICATIONS

Reed et al., "Autosomal Dominant Dementia with Widespread Neurofibrillary Tangles", *Ann. Neurol.*, 42(4):564–572(1997).

Schweers et al., "Oxidation of Cysteine–332 in the Repeat Domain of Microtubule–Associated Protein I Controls the in vitro Assembly of Paired Helical Filaments", *Proc. Natl. Acad. Sci. USA*, 92:8463–8467 (1995).

Spillantini et al., "Frontotemporal Dementia and Parkinsonism Linked to Chromosome 17: A New Group of Tauopathies", *Brain Pathology*, 8(2):387–402 (1998).

Wagner et al., "Cellular Phosphorylasation of Tau by GSK–3β Influences Tau Binding to Microtubules and Microtubule Organisation", *J. Cell Sci.*, 109:1537–1543 (1996).

* cited by examiner

PATHOGENIC TAU MUTATIONS

CROSS REFERENCE TO RELATED APPLICATIONS

This application claims priority from U.S. Provisional Application Ser. No. 60/097,492, filed Aug. 21, 1998, U.S. Provisional Application Ser. No. 60/087,942, filed Jun. 4, 1998, and U.S. Provisional Application Ser. No. 60/083,791, filed May 1, 1998.

STATEMENT AS TO FEDERALLY SPONSORED RESEARCH

Funding for the work described herein was provided in part by the Federal government, which has certain rights in the invention.

TECHNICAL FIELD

The invention relates to an isolated nucleic acid molecule that includes a tau gene sequence, wherein the tau gene sequence contains a mutation linked to a Tau pathology.

BACKGROUND OF THE INVENTION

Frontotemporal dementia and parkinsonism linked to chromosome 17 (FTDP-17) is characterized clinically by behavioral, cognitive, and motor disturbance. Historically, many cases of this disease have been described as Pick's disease. In the majority of families described to date, personality change is the presenting symptom, with initial behavioral changes accompanied by progressive cognitive impairment and sometimes parkinsonism. At autopsy, all patients with FTDP-17 display pronounced fronto-temporal atrophy and neuronal cell loss, gray and white matter gliosis, and superficial cortical spongiform changes. More variably, ballooned neurons, or Pick's cells, are present. In addition, most FTDP-17 cases show neuronal and/or glial inclusions that stain positively with antibodies raised against the microtubule associated protein Tau, although the Tau pathology varies considerably in both its quantity (or severity) and characteristics. Patients with FTDP-17 do not have Lewy bodies or, crucially, Pick bodies, which distinguishes them from classical Pick's disease cases. The disease is inherited as an autosomal dominant trait with age dependent penetrance. The age of onset can be highly variable but is usually between the ages of 45–65 years.

SUMMARY OF THE INVENTION

The invention is based on the discovery of mutations in the tau gene that are linked to Tau pathologies. Thus, the invention provides nucleic acid molecules that include such mutations, allowing animal models of neurodegenerative diseases to be developed. Identification of the mutations also provides methods for determining a diagnosis of neurodegenerative disease in a patient.

The invention features an isolated nucleic acid molecule including a tau gene sequence, wherein the molecule has a mutation linked to a Tau pathology. The nucleic acid molecule can be from about 15 nucleotides in length to full-length. The mutation can be located in an exon or in an intron. A mutation can be in exon 7, exon 9, exon 10, or in exon 13 and in particular embodiments, at a region encoding amino acids 152, 257, 272, 301, 389, or 406. In one embodiment, the mutation at amino acid 152 is a change from an alanine to a threonine residue, the mutation at amino acid 257 is a change from a lysine to a threonine residue, and the mutation at amino acid 272 is a change from a glycine residue to a valine residue. The mutation at amino acid 301 can be a change from a proline residue to a leucine residue. The mutation at amino acid 389 can be a change from a glycine to an arginine residue. The mutation of amino acid 406 can be a change from an arginine to a tryptophan residue. An additional mutation can include deletion of amino acid 280. The mutation also can be in a splice donor site region and, in a particular embodiment, can destabilize a stem-loop structure of the splice donor site region and can be in a region 13–16 nucleotides 3' of the exon 10 splice donor site.

The invention also features an isolated polypeptide encoded by a tau nucleic acid molecule of the invention. The polypeptides contain a mutation linked to a Tau pathology. Suitable mutations are described above.

The invention also features a transgenic non-human mammal including a nucleic acid construct. The nucleic acid construct includes a regulatory nucleic acid sequence operably linked to a nucleic acid sequence encoding a Tau polypeptide. Expression of the Tau polypeptide is linked to a Tau pathology in the transgenic non-human mammal. The transgenic non-human mammal can be a rodent, and in particular, a mouse. The regulatory nucleic acid sequence can be a brain-specific promoter. In one embodiment, the Tau polypeptide is human Tau polypeptide, and can be wild-type or can contain a mutation linked to a Tau pathology. The mutation can be, for example, at amino acid 152, 257, 272, 280, 301, 389, or 406. In other embodiments, the transgenic non-human mammal also includes a nucleic acid construct that includes a regulatory sequence operably linked to a nucleic acid sequence encoding a human amyloid precursor protein or a human presenilin-1 protein.

The invention also relates to a method for determining a diagnosis, prognosis, or risk of neurodegenerative disease in a patient. The method includes detecting a tau gene mutation in genomic DNA of the patient, wherein the mutation is linked to a Tau pathology. Mutations that are linked to Tau pathologies are described above.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A–1C are a segregation analysis (A), a schematic representation (B), and a sequence alignment (C) of tau mutations in FTDP-17.

DETAILED DESCRIPTION

Tau Mutations

In one aspect, the invention features an isolated nucleic acid molecule including a tau gene sequence, wherein the nucleic acid molecule has at least one mutation linked to a Tau pathology. As used herein, "isolated" refers to a sequence corresponding to part or all of the tau gene, but free of sequences that normally flank one or both sides of the tau gene in a mammalian genome. An isolated nucleic acid molecule can be, for example, a recombinant DNA molecule, provided one of the nucleic acid sequences normally found flanking that recombinant DNA molecule in a naturally-occurring genome is removed or absent. Thus, isolated nucleic acid molecules include, without limitation, a recombinant DNA that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a recombinant DNA molecule that is part of a hybrid or fusion nucleic acid molecule.

It will be apparent to those of skill in the art that a nucleic acid molecule existing among hundreds to millions of other nucleic acid molecules within, for example, cDNA or genomic libraries, or gel slices containing a genomic DNA restriction digest is not to be considered an isolated nucleic acid molecule.

A nucleic acid molecule of the invention typically is at least 15 nucleotides in length. For example, the nucleic acid molecule can be about 15 to 20, 20–50, 50–100, or 100–500 nucleotides in length. In other embodiments, the nucleic acid is full-length. The nucleic acid molecules can be in the form of RNA or in the form of DNA. The DNA can be double-stranded or single-stranded, circular or linear, and can be either coding or non-coding.

As used herein, "Tau pathology" refers to neurofibrillary tangles observed in brain, including one or more of the following: paired helical filaments (PHFs), straight Tau filaments, and any other type of Tau filament. Tau pathology also includes neuronal and/or glial inclusions or insoluble deposits that stain positively with anti-Tau antibodies. The tau gene encodes the microtubule associated protein Tau that is present in abnormal inclusions seen in FTDP-17 and is also the major component of the PHFs that make up the characteristic tangles seen in Alzheimer's disease (AD) and other neurodegenerative disorders. The human Tau protein found in brain is encoded by eleven exons. The sequence of the wild-type human tau gene is described by Andreadis, A. et al., *Biochemistry*, 31(43):10626–10633 (1992). The gene undergoes alternative splicing with exons 2, 3, and 10 absent from some forms of the mature brain tau mRNA. A total of six different tau mRNAs is generated as a result of this alternative splicing, with the mRNAs encoding proteins of 352–441 amino acids. The alternative splicing of exon 10 generates Tau protein with either three or four microtubule binding motifs that each are imperfect repeats of 31 or 32 residues. Tau protein containing three microtubule binding motifs is referred to herein as the three-repeat isoform, whereas Tau protein containing four microtubule binding motifs is referred to herein as the four-repeat isoform. Tau proteins containing three microtubule binding motifs (exon 10 −) form paired helical filaments, similar to those seen in the brains of AD patients, during in vitro aggregation experiments, while Tau proteins containing four microtubule binding motifs (exon 10+) form straight filaments.

The FTDP-17 locus maps to a 2 cM region on chromosome 17q21.1. As described herein, analysis of a large number of families with FTDP-17 and analysis of coding and non-coding regions of the tau gene revealed mutations linked to FTDP-17. The 11 tau coding exons and flanking intronic regions were initially sequenced in 38 individuals from families with fronto-temporal dementia from Scandinavia (9 families), the Netherlands (2 families), the USA (4 families), Australia (1 family), and from the Greater Manchester area of the UK (22 families). In this group, 7 families had previously displayed evidence for linkage to chromosome 17. The sequence analysis of the tau gene identified mutations in 5 of 7 families in which linkage to chromosome 17 had previously been indicated.

Mutations that are linked to Tau pathologies can be detected, for example, in exon 7, exon 9, exon 10, and exon 13. Amino acid mutations described herein are numbered from the longest Tau isoform, starting with the initial methionine. Amino acids have been designated herein by standard one letter and three letter abbreviations. Nucleotide mutations that correspond with the amino acid mutations described herein are numbered from the cDNA encoding the longest Tau isoform. Nucleotides have been designated by standard one letter abbreviations. Table 1 provides examples of Tau mutations that are linked to Tau pathologies, and the corresponding changes in nucleotide sequence. Other nucleotide sequences leading to the same amino acid changes can be ascertained from the known degeneracy of the genetic code.

TABLE 1

| Amino Acid Mutation | Corresponding Nucleotide Mutation |
|---|---|
| A152T | G454A |
| K257T | A770C |
| G272V | G815T |
| ΔK280 | ΔAAG(838–840) |
| P301L | C902T |
| G389R | G1166A |
| R406W | C1216T |

In exon 7, the mutation can include a change from an alanine to a threonine at residue 152 (i.e., A152T), which can result from a change at nucleotide 454 of a guanine to an adenine (i.e., G454A) in the tau gene sequence. A mutation in exon 9 from a lysine to a threonine at amino acid 257 (K257T) can result from a change of an adenine to a cytosine at nucleotide 770 of the tau gene sequence. Amino acid 272 can be changed from a glycine residue to a valine residue (G272V), a highly conserved residue within the microtubule binding domain encoded by exon 9, and is found in all Tau isoforms. The G272V mutation can result from a change of a thymine to a guanine at nucleotide 815 of the tau gene sequence. Amino acid 389 can be changed from a glycine to an arginine residue (G389R) in exon 13, with a corresponding change from a guanine to an adenine at nucleotide 1166. Amino acid 406, a highly conserved residue near the carboxy terminus of Tau, can be changed from an arginine to a tryptophan residue (R406W), with a corresponding change from a cytosine to a thymine at nucleotide 1216 of the tau gene.

Amino acid 301 can be changed from a proline residue to a leucine residue (P301L) in exon 10. The P301L substitution is a non-conservative substitution that occurs in a highly conserved region of the Tau protein sequence within one of the microtubule-binding domains. A proline residue is observed at the equivalent position in all species from which Tau has been cloned (see FIG. 1C). As a result, this substitution is highly likely to disrupt Tau microtubule binding. The P301L substitution only affects the four-repeat isoform, however, as exon 10 is spliced out of the mRNA that encodes the three-repeat exon 8–12 isoform.

Figures 2A, 2B:
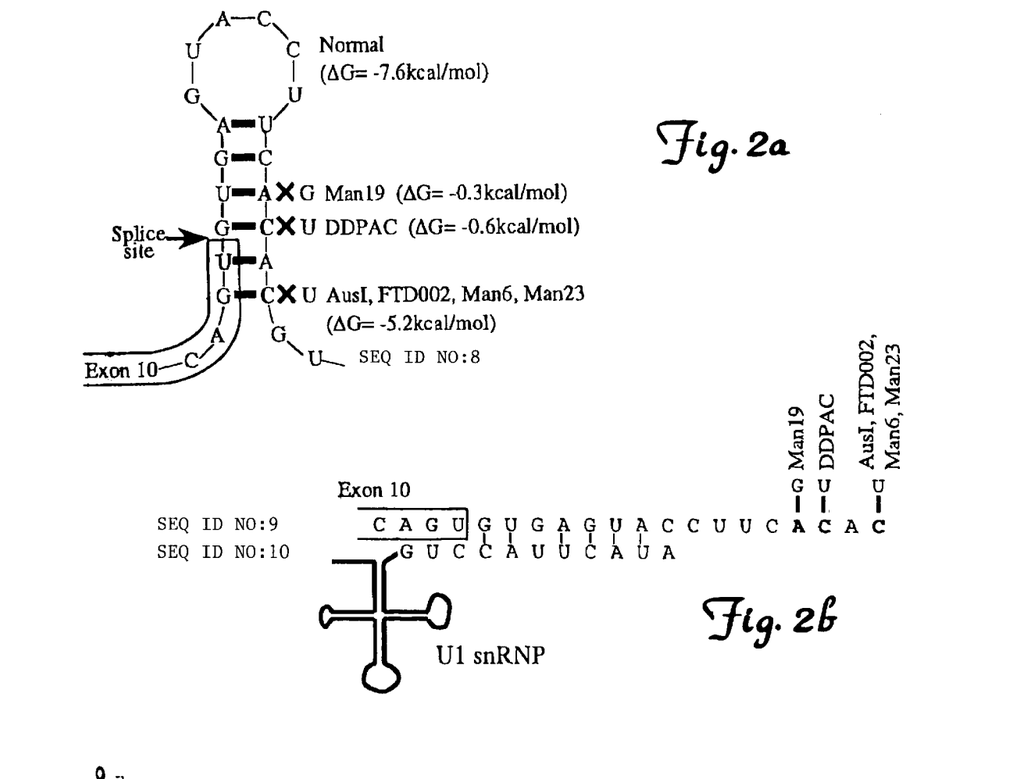
FIGS. 2A and 2B contain the sequence of the exon 10 splice donor site shown in a predicted stem-loop structure (A) and in linear form (B). The positions of three mutations are marked and the predicted free energy of the stem-loop with and without mutations is indicated. Predicted binding of the U1 SnRNP binding is thought to be blocked by the formation of the stem-loop.

A deletion of amino acid 280 was detected in a single Dutch family, with corresponding nucleotides 838–840 deleted from the tau gene sequence. In addition, mutations were detected in the exon 10 splice donor site region. For example, heterozygous mutations were identified in a cluster of four nucleotides 13–16 bp 3' of the exon 10 donor splice site (FIG. 2). No mutations were found in the tau gene in two families (HDDD2 and HFTD3).

The mutations described herein appear to cause FTDP-17, one of the major autosomal dominant loci associated with neurodegeneration. These data also indicate that a tau gene variant (V337M) in a family with FTDP-17 (Seattle A), Spillantini, M. G. et al., *Brain Path.,* 8:387–402 (1998), is likely pathogenic. The previous absence of mutations in other families had led to the suggestion that this might be a benign polymorphism. Most importantly, the identification of pathogenic missense and splice donor site mutations associated with FTDP-17 demonstrates for the first time that Tau dysfunction can lead to neurodegeneration. In addition, the nature of the splice-donor site mutations indicates that the relative levels of four-repeat and three-repeat Tau proteins are crucial to the correct functioning of Tau, at least in the brain. This is consistent with the observation that alternative splicing of exon 10 is known to be developmentally regulated. These mutations, by affecting the potential stem-loop structure in the exon 10 donor site, also reveal at least part of the mechanism by which alternative splicing of this exon is regulated. The existence of splice donor site, deletion, and missense mutations also may partially explain the variability observed in soluble Tau protein in FTDP-17.

The mutations in the exon 10 splice donor site are expected to lead to an increase in alternative splicing. A putative stem-loop structure containing a 12 base pair stem and a 6 base pair loop (FIG. 2A) spans the exon 10 splice donor site. All 3 of the mutations identified in this region occurred within the "stem" of this structure and would be expected to destabilize it. Short stem-loop structures can potentially sequester splice-donor sites and lead to alternative splice-donor site usage. Thus, the formation of the stem-loop structure might be involved in the regulation of exon 10 alternative splicing by blocking or slowing the use of this donor site, permitting the splicing of exon 9 to exon 11, and the generation of tau transcripts lacking exon 10. The result would be the maintenance of a precise ratio of transcripts with and without exon 10, and in turn, this would determine the ratio of four-repeat to three-repeat Tau protein. The mutations within the stem-loop associated with FTDP-17 are thought to destabilize this structure, promoting the use of the donor site and the inclusion of exon 10 in tau mRNA. This proposed mechanism would predict an increase in the proportion of tau transcripts containing exon 10 and thus an increase in the ratio of four-repeat to three-repeat protein isoforms. This mechanism for these mutations is consistent with the observation that soluble Tau in at least one FTDP-17 family displays a relative preponderance of Tau isoforms with four-repeats compared to control brains. In addition, the absence of this type of splice site mutation in many families (including those with missense mutations) is consistent with the observation that in other FTDP-17 families, the relative abundance of Tau isoforms with three- and four-repeats is similar to that seen in control brains.

Transgenic Non-human Mammals

The invention also features a transgenic non-human mammal including a nucleic acid construct. As used herein, "transgenic non-human mammal" includes the founder transgenic non-human mammals as well as progeny of the founders. The nucleic acid construct includes a regulatory nucleic acid sequence operably linked to a nucleic acid sequence encoding a Tau polypeptide. Nucleic acid constructs can be produced through standard recombinant DNA techniques. As used herein, "Tau polypeptide" refers to a Tau polypeptide of any length. Expression of the Tau polypeptide is linked to a Tau pathology in the transgenic non-human mammals. The Tau polypeptide can be, for example, encoded by a portion of an exon, a complete exon, or the full-length tau cDNA, and can be wild-type or can contain at least one mutation. Particularly useful mutations are described above.

Regulatory nucleic acid sequences provide expression of the Tau polypeptide in sufficient levels to produce a Tau pathology. Regulatory nucleic acid sequences include, for example, promoters, enhancers, inducible elements, and other upstream promoter elements. In particular embodiments, a regulatory nucleic acid sequence provides enhanced expression of the Tau polypeptide in the brain. A variety of regulatory nucleic acid sequences can be used to control expression of the Tau polypeptide. Non-limiting examples include the metallothionine promoter, the rat neural-specific enolase promoter, the human β-actin gene promoter, the human platelet derived growth factor B chain promoter, the rat sodium channel gene promoter, the human copper-zinc superoxide dismutase gene promoter, and the prion gene promoter.

Transgenic non-human mammals can be farm animals such as pigs, goats, sheep, cows, horses, and rabbits, rodents such as rats, guinea pigs, and mice, and non-human primates such as baboons, monkeys, and chimpanzees. Transgenic mice are particularly useful.

Various techniques known in the art can be used to introduce nucleic acid constructs into non-human mammals to produce the founder lines of the transgenic non-human mammals. Such techniques include, but are not limited to, pronuclear microinjection (U.S. Pat. No. 4,873,191), retrovirus mediated gene transfer into germ lines (Van der Putten et al., *Proc. Natl. Acad. Sci. USA,* 82:6148, 1985), gene targeting into embryonic stem cells (Thompson et al., *Cell,*

56:313, 1989), electroporation of embryos (Lo, *Mol. Cell. Biol.*, 3:1803, 1983), and transformation of somatic cells in vitro followed by nuclear transplantation (Wilmut et al., *Nature*, 385(6619):810–813, 1997; and Wakayama et al., *Nature*, 394:369–374, 1998).

Once transgenic non-human mammals have been generated, expression of the Tau polypeptide can be assessed using standard techniques. Initial screening can be accomplished by Southern blot analysis or polymerase chain reaction (PCR) techniques to determine whether or not integration of the transgene has taken place. See, for example, sections 9.37–9.52 of Sambrook et al., 1989, *"Molecular Cloning, A Laboratory Manual"*, second edition, Cold Spring Harbor Press, Plainview; N.Y., for a description of Southern analysis.

PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, R. *Genetic Engineering News*, 12(9):1 (1992); Guatelli et al., *Proc. Natl. Acad. Sci. USA*, 87:1874–1878 (1990); and Weiss, R., *Science*, 254:1292 (1991).

Expression of the nucleic acid sequence encoding a Tau polypeptide in the tissues of the transgenic non-human mammals can be assessed using techniques that include, but are not limited to, Northern blot analysis of tissue samples obtained from the animal, in situ hybridization analysis, and reverse-transcriptase PCR (RT-PCR). A Tau pathology can be manifested as, for example, neurofibrillary tangles or neuronal and/or glial inclusions or insoluble deposits that stain positively with anti-Tau antibodies, as described above. Anti-Tau antibodies are available commercially from, for example, Sigma Chemical Company (St. Louis, Mo.). Anti-Tau antibodies that are sensitive to phosphorylated epitopes of Tau are available from Innogenetics (Belgium).

In one embodiment, transgenic mice further include a nucleic acid construct encoding a human amyloid precursor protein (APP) or human presenilin-1 (PS-1) protein. The nucleic acid sequence of human APP has GenBank Accession No. D87675 g2429080. The nucleic acid sequence encoding human PS-1 protein has GenBank Accession Nos. L76518–L76528. Expression of APP or PS-1 can enhance the Tau pathology observed with expression of Tau polypeptides. The ratio of Tau polypeptide containing four microtubule binding motifs to Tau polypeptide containing three microtubule binding motifs (i.e, ratio of four-repeat to three-repeat isoform) plays a role in the correct functioning of the Tau protein. As described herein, the splicing mutations affect the relative levels of four-repeat Tau and three-repeat Tau proteins, which may have important implications for the modeling of Alzheimer's disease since mouse brains contain nearly all four-repeat Tau (almost the direct opposite of the human brain). The mouse tau gene lacks a "stable" stem-loop structure to regulate alternate splicing of exon 10 leading to the presence of a single isoform. Current transgenic mouse models of Alzheimer's disease expressing APP at high levels develop amyloid plaques (Aβ plaques) and contain hyper-phosphorylated Tau polypeptide, but do not contain Tau positive tangles or exhibit significant cell loss.

Therefore, it appears that there is a difference in the response of mouse and human neurons to an amyloid insult. Given the evidence of Tau involvement in neurodegeneration, provided by the mutations described herein, and the dramatic difference in the ratio of four-repeat and three-repeat Tau isoforms in the mouse and human brains, Tau polypeptide seems a likely candidate to explain the difference in the response of mouse and human neurons to amyloid. This hypothesis is further strengthened by the observation, again from the splice site mutations described herein, that the ratio of four-repeat to three-repeat Tau is indeed important to Tau function. Disturbances in this ratio can lead to neurodegeneration. The fact that mice have a preponderance of four-repeat Tau isoform also may be significant since four-repeat Tau protein binds more tightly to microtubules (compared to three-repeat Tau) and produces more stable microtubules. It is possible therefore that the mouse is better able to withstand the process induced by amyloid (Aβ) that leads to neurodegeneration and Alzheimer's disease in humans.

Transgenic mice expressing a Tau polypeptide and APP or PS-1 can be produced by crossing transgenic mice overexpressing human three-repeat tau cDNAs (wild type cDNAs or cDNAs containing pathogenic mutations) with mice overexpressing human APP and/or human PS-1 cDNAs. Transgenic mice overexpressing human APP or human PS-1 are described, for example, in WO 97/48792 and WO 97/27296, respectively. See, WO 98/17782 for a description of transgenic mice containing mutant APP and mutant PS-1 transgenes. Alternatively, a single line of transgenic mice can be produced by initially preparing the mice using the appropriate constructs. Increasing the proportion of three-repeat Tau in the mouse brain may lead to greater susceptibility to amyloid insults, tangle formation, and cell death, generating an improved model of Alzheimer's disease and providing insight into the disease process.

Methods for Diagnosing Neurodegenerative Diseases

In another aspect, the invention features a method for determining a diagnosis, prognosis, or risk of neurodegenerative disease in a patient. The method includes detecting a tau gene mutation in genomic DNA of the patient, wherein the mutation is linked to a Tau pathology. Neurodegenerative diseases, include, for example, FTDP-17, Pick's disease, Progressive Supranuclear Palsy (PSP), Corticobasal degeneration (CBD), lytico and bodig disease of Guam, variants of AD with straight tau filaments, and any other neurodegenerative diseases in which Tau pathology is a major feature. Tau pathology includes neurofibrillary tangles observed in brain, including one or more of the following: paired helical filaments (PHFs), straight Tau filaments and any other type of Tau filament. Tau pathology also includes neuronal and/or glial inclusions or insoluble deposits that stain positively with anti-Tau antibodies.

Tau gene mutations can be detected by various methods. Mutations can be detected, for example, by sequencing exons and introns of the tau gene, restriction fragment length polymorphisms (RFLP) analysis, PCR-RFLP analysis, allele-specific hybridizations, mutation specific polymerase chain reactions (MSPCR), or by single stranded conformational polymorphism (SSCP) detection.

Genomic DNA is generally used in the detection of tau gene mutations. Genomic DNA typically is extracted from peripheral blood samples, but also can be extracted from, for example, mucosal scrapings of the lining of the mouth. Brain tissue obtained from an autopsy also can be used for post-mortem diagnosis. Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.), and the A.S.A.P.™ Genomic DNA isolation kit (Boehringer Mannheim, Indianapolis, Ind.).

For example, exons and introns of the tau gene can be amplified through PCR and then directly sequenced. This method can be varied, including using dye primer sequencing to increase the accuracy of detecting heterozygous samples. Alternatively, a nucleic acid molecule can be selectively hybridized to the PCR product to detect a gene variant. Hybridization conditions are selected such that the nucleic acid molecule can specifically bind the sequence of interest, e.g., the mutant nucleic acid sequence. Such hybridizations typically are performed under high stringency as many mutations include only a single nucleotide difference. High stringency conditions can include the use of low ionic strength solutions and high temperatures for washing, for example, 0.015 M NaCl/0.0015 M sodium citrate (0.1× SSC), 0.1% sodium dodecyl sulfate (SDS) at 60° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2× SSC and 0.1% SDS. Hybridization conditions can be adjusted to account for unique features of the nucleic acid molecule, including length and sequence composition.

PCR-RFLP analysis can be performed in the following manner. If a tau mutation introduces a restriction site, restriction digest with the particular restriction enzyme can differentiate wild-type tau from mutated tau. For example, missense mutation of a proline to leucine at amino acid 301 can be detected by BstNI or SmaI digestion of exon 10 PCR products. The mutant allele contains a BstNI site, whereas the normal allele contains a SmaI site. The exon 10 splice donor +16 mutation can be detected by NspI digestion. Again, the mutant allele is cleaved while the normal allele is not cleaved by NspI. The exon 10 splice donor +13 and +14 mutations eliminate an AflIII site from the amplification product. For tau mutations that do not alter a common restriction site, primers can be designed that introduce a restriction site when the mutation is present, or when the wild-type sequence is present.

PCR conditions and primers can be developed that amplify a product only when the mutation is present or only when the wild-type tau is present (MSPCR or allele-specific PCR). For example, patient DNA and a control can be amplified separately using either a wild-type primer or a primer specific for the mutation. Each set of reactions then is examined for the presence of amplification products using standard methods to visualize the DNA. For example, the reactions can be electrophoresed through an agarose gel and DNA visualized by staining with ethidium bromide or other DNA intercalating dye. In DNA samples from heterozygous patients, reaction products would be detected in each reaction. Patient samples containing solely wild-type tau would have amplification products only in the reaction using the wild-type primer. Similarly, patient samples containing solely mutated tau would have amplification products only in the reaction using the variant primer.

Mismatch cleavage methods also can be used to detect differing sequences by PCR amplification, followed by hybridization with the wild-type sequence and cleavage at points of mismatch. Chemical reagents, such as carbodiimide or hydroxylamine and osmium tetroxide can be used to modify mismatched nucleotides to facilitate cleavage.

Alternatively, the ratio of exon 10+ and exon 10− RNA can be measured and used for determining a diagnosis, prognosis or risk of neurodegenerative disease in a patient. For example, reverse transcriptase PCR (RT-PCR) can be performed on total RNA isolated from a patient. After amplification, PCR products can be resolved into fragments with and without exon 10, and the molar ratio of exon 10+ to exon 10− RNA can be determined using densitometry. Patients with an increase in the proportion of exon 10+ RNA can have a mutation in the splice donor sites of the tau gene.

The invention will be further described in the following examples, which do not limit the scope of the invention described in the claims.

EXAMPLES

Example 1

General Methods:

Tau Gene Sequencing

Tau exons were PCR amplified from genomic DNA from family members with primers designed to flanking intronic sequence. Each reaction contained approximately 0.8 pM of each primer and 1 unit of Taq "Gold" polymerase (Perkin Elmer). Amplification was performed using a 60° C. to 50° C. touchdown protocol over 35 cycles, with a final extension of 72° C. for 10 min. PCR products were purified using a Qiagen PCR kit and their concentration estimated on an agarose gel. DNA (100 ng) for each exon was sequenced on both strands using the dRhodamine dye terminator cycle sequencing kit (Perkin Elmer) and relevant PCR primers. Sequencing was performed on an ABI377 automated sequencer. Heterozygote base calls were made using Factura software (Perkin Elmer) and sequence alignment was performed by Sequence Navigator (Perkin Elmer).

Mutation Detection

Mutations were detected in families (for segregation analysis) and controls using sequencing as described above, or PCR-RFLP analysis. Missense mutation P301L was detected by BstNI or SmaI digestion of exon 10 PCR products. The mutant allele contained a BstNI site, whereas the normal allele contained a SmaI site. The exon 10 splice donor +16 mutation was detected by NspI digestion, in which the mutant allele was cleaved by NspI. In contrast, the exon 10 splice donor +13 and +14 mutations eliminated an AflIII site from the amplification product. After digestion, genotyping was performed using 3% Metaphor (FMC) agarose gels.

RT-PCR Analysis of Exon 10 Alternative Splicing

Total RNA was prepared from a section of frontal lobe from seven normal brains and from the frontal lobes of four FTDP-17 brains using the Trizol reagent and protocol (Life Technologies). Two of the FTDP-17 brains were from families with splice donor site mutations (DDPAC and Aus1) and two were from family FTD003 with the P301L point mutation. Reverse transcription was performed using the Superscript preamplification kit (Life Technologies) on 1–4 µg of brain RNA with an oligo dT primer. PCR was performed between exon 9 (Forward 5'-ATCGCAGCGGCTACAGCAG-3', SEQ ID NO:1) and exon 11 (Reverse 5'-TGGTTTATGATGGATGTTGCC-3', SEQ ID NO:2) and between exon 9 and exon 13 (Reverse 5'-TCTTGGCTTTGGCGTTCTC-3', SEQ ID NO:3). Preliminary PCR reactions were performed using a range of amplification cycles to determine the optimum number of cycles for this analysis. Based on the results of this initial study, 32 cycles were used in subsequent experiments. After amplification, PCR products were electrophoresed through a 2% Metaphor agarose gel where they resolved into two major fragments (327 and 418 bp, exon 9–11, 487 bp and 578 bp, exon 9–13) corresponding to tau transcripts with and without exon 10. The molar ratio of exon 10+ to exon 10– RNA was determined using a Kodak DC120 camera kit and ID Image Gel densitometry software. Three independent PCR reactions (for both Ex9–11 and Ex9–13) were used to determine the mean ratio for each brain. After ratios were determined for all experiments, a comparison of FTDP-17 mutant splice site brains was made against normal and FTDP-17 brains with the P301L point mutation using single tailed t-tests.

Exon-trapping Analysis of Exon-10 Splicing

Mutant and wild-type versions of tau exon 10 were amplified from the DNA of patients with each of the three different splice mutations (+13, +14, and +16) and from normal individuals. PCR products contained exon 10 and approximately 40 bp of flanking intron sequence at either end. PCR products were cloned into the splicing vector pSPL3b using XhoI and PstI sites incorporated into the amplification products. Mutant and wild-type constructs were identified by sequence analysis. For exon trapping, the exon-trapping system of Life-Technologies was used. Briefly, COS-7 cells were transfected in duplicate with 1 µg of each construct using LipofectACE reagent (Life Technologies). Cells were collected 24 h post-transfection and RNA prepared using the Trizol reagent (Life Technologies). First-strand synthesis and nested PCR were done using reagents supplied with the system and conditions described in manufacturer's instructions, except that BstX1 digestion of primary PCR products was excluded. To verify that RT-PCR was quantitative, different amounts of primary PCR template (1 to 5 µl) were used and the total number of amplification cycles was varied (30–35 cycles). PCR products were analyzed on 3% Metaphor (FMC) gels. Identity of RT-PCR products was confirmed by sequencing.

Example 2

Figure 1A:
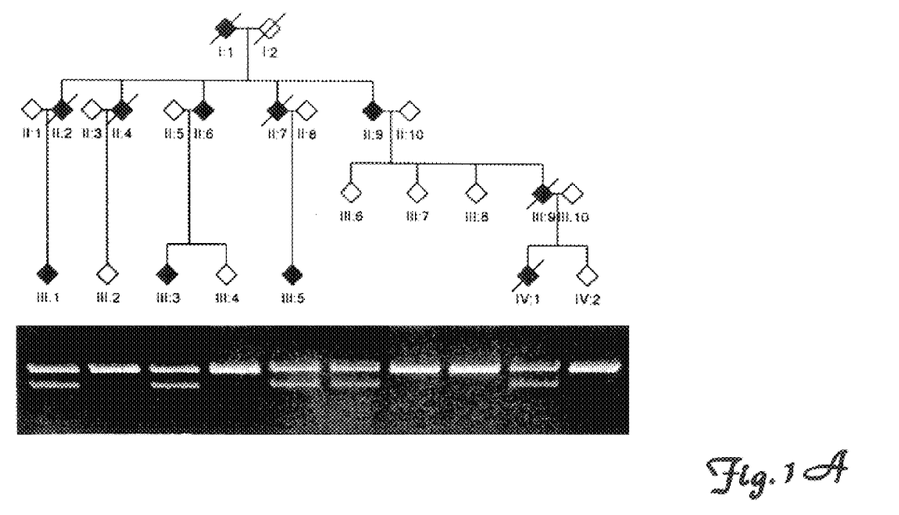
FIG. 1A is a segregation analysis of the exon 10 splice donor +16 mutation in the AusI kindred. The presence of the mutation is indicated by an extra band at 148 bp on the agarose gel, while the normal allele is represented by a band at 200 bp. Individual III.6 has the mutation and the disease haplotype despite being currently unaffected.
Figure 1B:
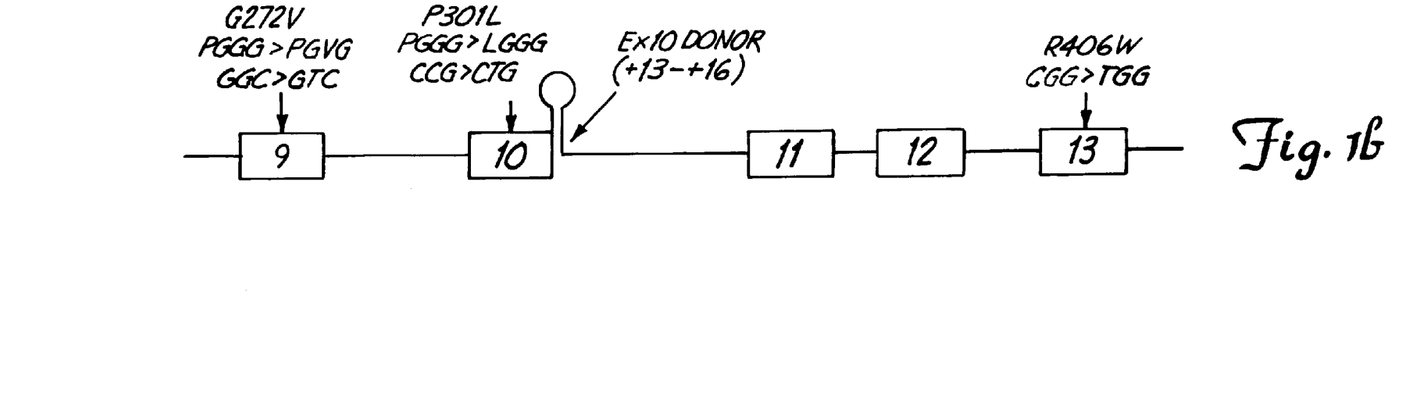
FIG. 1B is a schematic representation of the tau gene (exons 9–13) displaying the relative locations of missense mutations in the coding region and in the splice donor site. The effect of two missense mutations, G272V and P301L, on the PGGG motif in the microtubule binding domains encoded by exon 9 and 10, respectively, is shown.
Figure 1C:
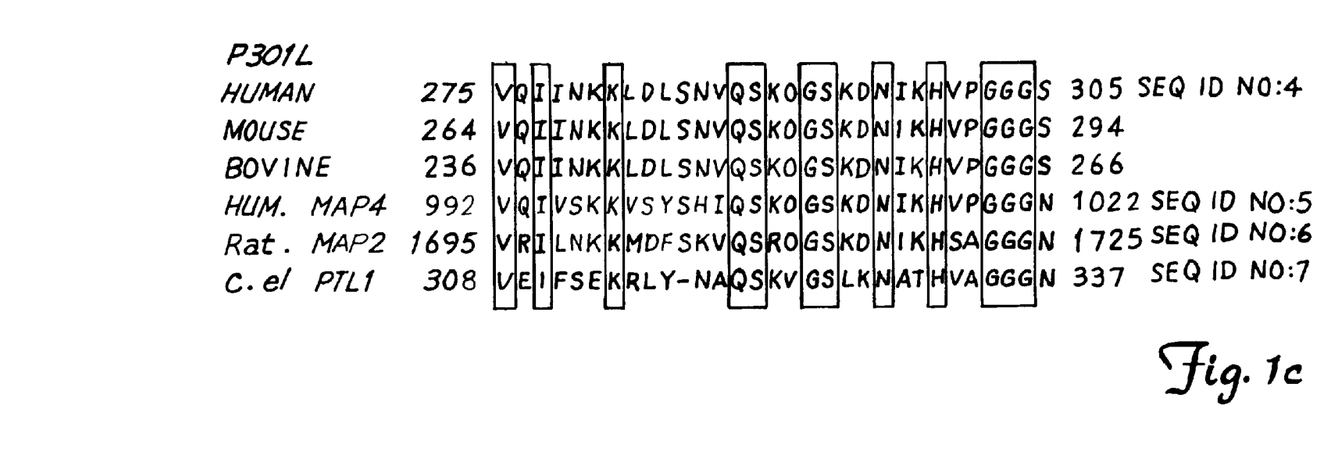
FIG. 1C is a sequence alignment of the microtubule binding domain encoded by exon 10 with the equivalent regions from mouse and cow and from the human and rat microtubule associated protein 4 (MAP4). The location of the P301L missense mutation is indicated above the alignment.

Detection of Pathogenic Mutations in Tau:

A missense mutation was detected in exon 10 in two families (Table 2); a large Dutch kindred, Hereditary Frontal Temporal Dementia I (HFTDI) that had previously been linked to chromosome 17, and a small U.S. kindred (FTD003). This mutation results in the substitution of proline to leucine at codon 301 (P301L), numbered from the longest isoform (FIG. 1C).

TABLE 2

Families with segregating mutations within the tau gene

| Family ID | Origin (founder) | Affected (PM confirmed) | Generations | Mean onset age (years) | Mutation |
|---|---|---|---|---|---|
| HFTD2* | Netherlands | 34(15) | 7 | 47 | G272V |
| HFTD1* | Netherlands | 49(14) | 5 | 50 | P301L |
| FTD003 | USA | 3(2) | 2 | 45–50 | P301L |
| Man19 | UK | 3(1) | 2 | 65 | Ex 10 splice + 13 |
| DDPAC* | Ireland | 13(6) | 3 | 44 | Ex 10 splice + 14 |
| AusI* | Australia(UK) | 28(5) | 5 | 53 | Ex 10 splice + 16 |
| FTD002* | USA | 3(1) | 2 | 40 | Ex 10 splice + 16 |
| Man6 | UK | 2(1) | 1 | 48 | Ex 10 splice + 16 |
| Man23* | UK | 10(2) | 3 | 51 | Ex 10 splice + 16 |
| FTD004 | USA | 10(2) | 4 | 55 | R406W |
| HFTD4 | Netherlands | 2 | 2 | 53 (one patient) | Deletion of K280 |

*Families that displayed prior evidence of genetic linkage to chromosome 17.

A G272V mutation was found in a second large Dutch kindred HFTD2 (Table 2) that had originally been described as having hereditary Pick's disease indicating the considerable clinical overlap between Pick's disease and FTDP-17. The G272V mutation also affects a highly conserved residue within a microtubule binding domain, encoded by exon 9, and again this mutation affects the specific region that interacts with the microtubule. Indeed, within the imperfect repeat sequence that makes up the four microtubule binding domains, the G272V and P301L mutations affect the residue equivalent to G303, that are separated by only one residue. Thus, for P301L, the PGGG motif in the binding repeat becomes LGGG, and for G272V, the motif becomes PGVG. In contrast to the P301L mutation (exon 10), the G272V mutation (exon 9) will affect all Tau isoforms. The G272V and P301L mutations were found to segregate with disease in each of the relevant families. Both mutations were absent from 192 Dutch controls and the P301L mutation also was absent from a further 150 Caucasian control individuals from a Florida patient series. Thus, these data taken together indicate that the G272V and the P301L mutations that likely affect Tau microtubule binding are pathogenic in HFTD2 (G272V) and in HFTD1 and FTD003 (P301L).

A third tau missense mutation (R406W) was detected in exon 13, in a single family from the USA (FTD004). It alters a highly conserved residue near the C-terminus. The R406W mutation segregates with the disease in this family and was absent from 150 controls collected in the USA. The distribution of Tau positive inclusions in FTD004 meets NINDS neuropathologic criteria for PSP. Electron microscopy revealed, however, that the Tau filaments in this family are AD-like PHFs and not the straight Tau filaments normally observed in PSP. The clinical phenotype includes memory loss and personality change and would be unusual for PSP. The neuropathological phenotype in this family also is highly similar to that of the lytico and bodig diseases of Guam. The pathogenic mechanism of R406W remains unclear. The proximity of this mutation to key residues that are phosphosphorylated in PHF Tau (Ser396, Ser404), however, suggests that this mutation may in some way influence Tau phosphorylation and thus the formation of PHFs.

In addition to the missense mutations, three heterozygous mutations were observed in a cluster of 4 nucleotides 13–16 bp 3' of the exon 10 splice donor site (FIG. 2). Six families (Table 2) had mutations at these three sites including four families which had previously displayed evidence for linkage to chromosome 17 (DDPAC, AusI, FTD002, and Man23). In each of the six families, the relevant mutation was found to segregate with disease (FIG. 1a). None of the 3 intronic mutations were observed in 150 USA and 23 UK caucasian control individuals. These data, together with the presence of the mutations in such a tight cluster in close proximity to the exon 10 splice donor site and the number of affected FTD families (6), indicates that these variants were pathogenic.

Example 3

Figure 2C:
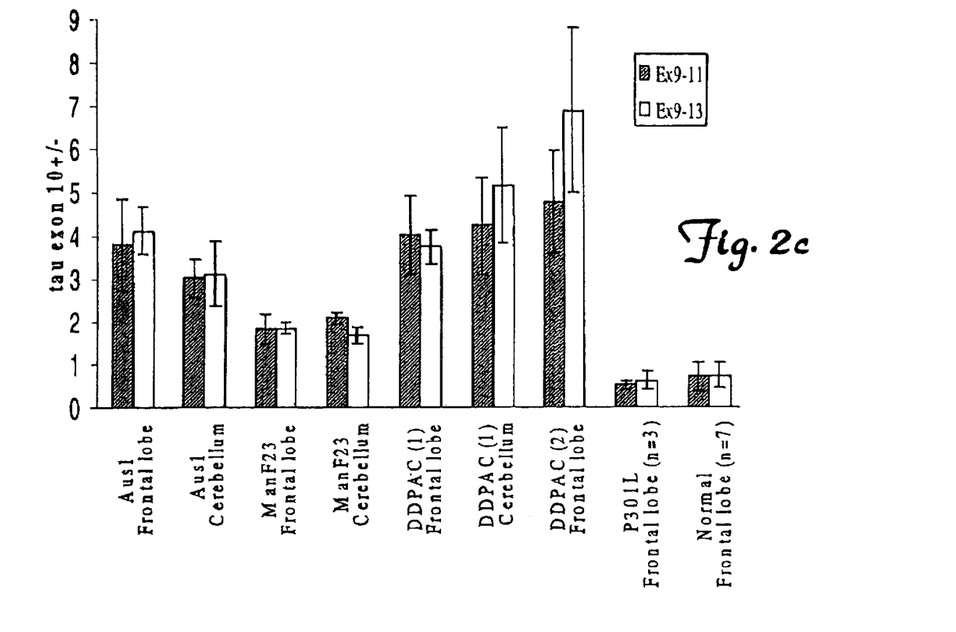
FIG. 2C is a graph representing the RT-PCR analysis of the molar ratio between tau mRNA + and − exon 10 in different brains. Amplification results from exons 9–11 are shown as white bars and from exons 9–13 as hatched bars.

Ratio of Tau Exon $10^+$RNA to Exon $10^-$ RNA in Patients:

RT-PCR was used to estimate the ratio of tau exon 10 + RNA to exon 10 − RNA in four FTDP-17 brains. Two of the brains were from families with splice donor site mutations, DDPAC and AusI, and two were from the FTD003 family with the P301L mutation. RT-PCR was performed to amplify a product between exon 9 and exon 11 and, in a separate reaction, between exon 9 and exon 13. Both these amplifications generate two products, one corresponding to tau transcripts containing exon 10 and one corresponding to tau transcripts in which exon 10 is skipped. In both PCRs, the brains containing the splice mutations (DDPAC and AusI) gave a 2–4 fold higher proportion of tau exon 10 + RNA as compared with 7 control brains (FIG. 2C). RNA from frontal lobe (4 cases) and cerebellum (3 cases) from FTDP-17 brains with splice site mutations (DDPAC (2 brains), ManF23 and AusI) have molar ratios >1.6 (left 14 bars of FIG. 2C). RNA from the frontal lobes of normal brains (n=7) and three FTDP-17 brains with the P30IL mutations have ratios <0.8 (right 4 bars of FIG. 2C). The FTDP-17 brains in which splice mutations were not identified gave similar ratios to that of the controls (FIG. 2C), indicating that the increase in the ratio in the splice site mutation brains was not simply an inevitable consequence of the disease process. The increase in the proportion of exon 10 + tau RNA (2–4 fold) is most consistent with the complete or virtually complete elimination of exon 10 − tau mRNA generated from the mutant allele.

Example 4

Impact of 5' Splice Site Mutations on Alternative Splicing:

Exon-trapping assays were used to test the effect of the 5' splice site mutations on alternative splicing of tau exon 10. Wild-type and three mutant versions (+13, +14, and +16) versions of exon 10 were analyzed. These nucleic acid molecules, which included approximately 40 bp of intronic sequence at either end, were amplified, and cloned into the splicing vector pSPL3b, which contains exons from the rabbit β-globin and HIV tat genes. A multiple cloning site in an intron between the two tat exons allows test DNA to be introduced. An SV40 promoter in pSPL3b drives the generation of artificial mRNAs when the construct is transfected into COS7 cells, trapping any functional exons in the cloned DNA between the two tat exons, so they can be detected by RT-PCR. Data from all constructs were derived from two independent transfections. The identity of all RT-PCR products was verified by sequence analysis.

Figure 3A:
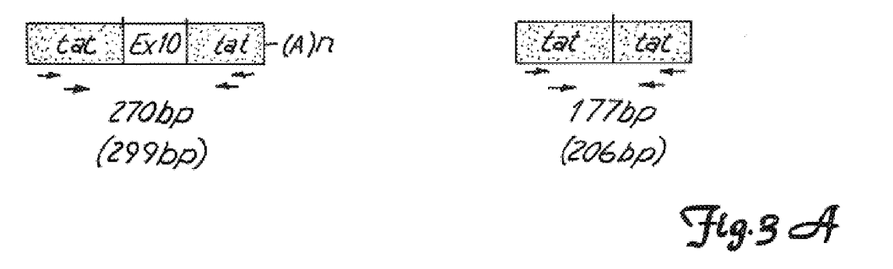
FIGS. 3A and 3B are a schematic representation of major RT-PCR products generated by exon trapping analysis of tau exon 10 (A) and results of exon trapping analysis of tau exon 10 (B).

PCR products result from splicing of pSPL3b vector-derived tat exons with (270 bp) and without (177 bp) tau exon 10. The sizes of minor products 299 bp and 206 bp in length correspond to exon 10+ and exon 10− transcripts, respectively, into which 29 bp of additional vector sequence was incorporated into the 5' tat exon, are shown in brackets. This artifact does not affect the splicing of exon 10 between the two tat exons. The position of nested RT-PCR primers is indicated by arrows.

Figure 3B:
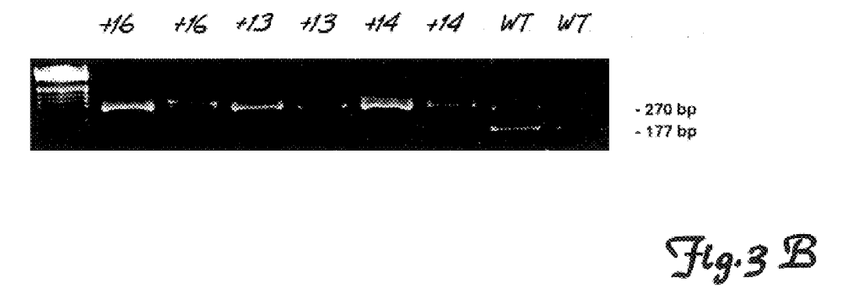

Wild-type constructs gave strongest signals from bands (177 bp, 206 bp) corresponding to exon 10− vector-only splicing, with the most prominent being at 177 bp (exon 10− RNA). Weaker products at 270 bp corresponded to exon 10+ transcripts. With the mutant constructs, tat to tat spliced vector-only transcripts (177 bp) were greatly reduced, consistent with increased usage of the exon-10 5' splice site. 5' splice site mutants (+16, +13, and +14) gave strongest signals corresponding to exon 10+ transcripts (270 bp, 299 bp), with products corresponding to exon 10− vector-only splicing (177 bp, 206 bp) dramatically reduced and virtually absent in +13 and +14. These results show that the 5'-splice-site mutants increase splicing of exon 10 in vitro. The data suggest that the splice donor site mutations observed in 6 FTDP-17 families act by increasing the proportion of tau mRNA that contains exon 10 and which encodes the four-repeat Tau protein isoform.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule encoding a human Tau polypeptide, said polypeptide having a mutation that is associated with a Tau pathology, wherein said mutation is selected from the group consisting of threonine residue at amino acid 257, a valine residue at amino acid 272, a deletion of amino acid 280, a leucine residue or a serine residue at amino acid 301, an arginine residue at amino acid 389, and a tryptophan residue at amino acid 406.

2. The isolated nucleic acid molecule of claim 1, wherein said nucleic acid molecule is at least 15 nucleotides in length.

3. The isolated nucleic acid molecule of claim 1, wherein said nucleic acid molecule encodes a full-length human Tau polypeptide having 352, 383, 381, 410, 412, or 441 amino acid residues.

4. The isolated nucleic acid molecule of claim 1, wherein said mutation is a leucine residue at amino acid 301.

5. The isolated nucleic acid molecule of claim 1, wherein said mutation is an arginine residue at amino acid 389.

6. The isolated nucleic acid molecule of claim 1, wherein said mutation is a tryptophan residue at amino acid 406.

7. The isolated nucleic acid molecule of claim 1, wherein said mutation is a valine residue at amino acid 272.

8. The isolated nucleic acid molecule of claim 1, wherein said mutation is a threonine residue at amino acid 257.

9. The isolated nucleic acid molecule of claim 1, wherein said mutation is a deletion of amino acid residue 280.

10. An isolated polypeptide encoded by the isolated nucleic acid molecule of claim 1.

11. The isolated polypeptide of claim 10, wherein said polypeptide comprises a leucine residue at amino acid 301.

12. The isolated polypeptide of claim 10, wherein said polypeptide comprises an arginine residue at amino acid 389.

13. The isolated polypeptide of claim 10, wherein said polypeptide comprises a tryptophan residue at amino acid 406.

14. The isolated polypeptide of claim 10, wherein said polypeptide comprises a valine residue at amino acid 272.

15. The isolated polypeptide of claim 10, wherein said polypeptide comprises a threonine residue at amino acid 257.

16. The isolated nucleic acid molecule of claim 1, wherein said mutation is a serine residue at amino acid 301.

17. An isolated nucleic acid molecule comprising a human tau gene sequence, said tau gene sequence having a mutation linked to a Tau pathology, wherein said mutation is in a region 13–16 nucleotides 3' of the exon 10 splicer donor site region of said tau gene sequence.

18. The isolated nucleic acid molecule of claim 17, wherein said mutation destabilizes a step-loop structure of said splice donor site region.

19. A method for determining a diagnosis, prognosis or risk of a Tau pathology in a patient, said method comprising detecting a tau gene mutation in genomic DNA of said patient, wherein said mutation is in an exon of said tau gene or in a region 13–16 nucleotides 3' of the exon 10 splice donor site of said tau gene, wherein said mutation in said exon results in a deletion of amino acid 280, a threonine residue at amino acid 257, a valine residue at amino acid 272, a leucine residue or a serine residue at amino acid 301, an arginine residue at amino acid 389, or a tryptophan residue at amino acid 406 of a human Tau polypeptide, and wherein said mutation is associated with said Tau pathology.

20. The method of claim 19, wherein said mutation is a leucine residue at amino acid 301.

21. The method of claim 19, wherein said mutation is a arginine residue at amino acid 389.

22. The method of claim 19, wherein said mutation is a tryptophan residue at amino acid 406.

23. The method of claim 19, wherein said mutation is a valine residue at amino acid 272.

24. The method of claim 19, wherein said mutation is a threonine residue at amino acid 257.

25. The method of claim 19, wherein said mutation is a serine residue at amino acid 301.

26. The method of claim 19, wherein said mutation is a serine residue at amino acid 301.

* * * * *

SEQUENCE LISTING

<160> NUMBER OF SEQ ID NOS: 7

<210> SEQ ID NO 1
<211> LENGTH: 19

```
<212> TYPE: DNA
<213> ORGANISM: Artificial Sequence
<220> FEATURE:
<223> OTHER INFORMATION: primer

<400> SEQUENCE: 1
atcgcagcgg ctacagcag                                                    19

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tggtttatga tggatgttgc c                                                 21

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
tcttggcttt ggcgttctc                                                    19

<210> SEQ ID NO 4
<211> LENGTH: 31
<212> TYPE: PRT
<213> ORGANISM: Homo sapiens, Mus musculus, Bos taurus

<400> SEQUENCE: 4

Val Gln Ile Ile Asn Lys Lys Leu Asp Leu Ser Asn Val Gln Ser Lys
 1               5                  10                  15

Cys Gly Ser Lys Asp Asn Ile Lys His Val Pro Gly Gly Gly Ser
                20                  25                  30

<210> SEQ ID NO 5
<211> LENGTH: 31
<212> TYPE: PRT
<213> ORGANISM: Homo sapiens

<400> SEQUENCE: 5

Val Gln Ile Val Ser Lys Lys Val Ser Tyr Ser His Ile Gln Ser Lys
 1               5                  10                  15

Cys Gly Ser Lys Asp Asn Ile Lys His Val Pro Gly Gly Gly Asn
                20                  25                  30

<210> SEQ ID NO 6
<211> LENGTH: 31
<212> TYPE: PRT
<213> ORGANISM: Rattus norvegicus

<400> SEQUENCE: 6

Val Arg Ile Leu Asn Lys Lys Met Asp Phe Ser Lys Val Gln Ser Arg
 1               5                  10                  15

Cys Gly Ser Lys Asp Asn Ile Lys His Ser Ala Gly Gly Gly Asn
                20                  25                  30

<210> SEQ ID NO 7
<211> LENGTH: 30
<212> TYPE: PRT
```

-continued

```
<213> ORGANISM: Caenorhabditis elegans

<400> SEQUENCE: 7

Val Glu Ile Phe Ser Glu Lys Arg Leu Tyr Asn Ala Gln Ser Lys Val
1               5                   10                  15

Gly Ser Leu Lys Asn Ala Thr His Val Ala Gly Gly Gly Asn
            20                  25                  30
```